United States Patent [19]
Peterson

[11] Patent Number: 5,823,986
[45] Date of Patent: Oct. 20, 1998

[54] PERFUSION SYSTEM

[75] Inventor: Donovan D. Peterson, Long Lake, Minn.

[73] Assignee: Medtronic, Inc., Minneapolis, Minn.

[21] Appl. No.: 385,264

[22] Filed: Feb. 8, 1995

[51] Int. Cl.⁶ ............................................. A61M 37/00
[52] U.S. Cl. ................................................ 604/4; 422/44
[58] Field of Search .............................. 604/4–6; 435/2; 422/44–48

[56] References Cited

U.S. PATENT DOCUMENTS

| | | | |
|---|---|---|---|
| Re. 32,711 | 7/1988 | Dickens et al. ................ | 210/304 |
| 3,890,969 | 6/1975 | Fischel ........................ | 128/214 R |
| 3,896,733 | 7/1975 | Rosenberg .................... | 128/214 R |
| 4,131,432 | 12/1978 | Siposs ......................... | 422/45 |
| 4,490,331 | 12/1984 | Steg, Jr. ...................... | 422/46 |
| 4,828,543 | 5/1989 | Weiss et al. ................... | 604/6 |
| 4,923,438 | 5/1990 | Vasconcellos et al. ......... | 604/4 |
| 5,039,482 | 8/1991 | Panzani et al. ................ | 422/46 |
| 5,158,533 | 10/1992 | Strauss et al. ................ | 604/4 |
| 5,188,604 | 2/1993 | Orth ............................ | 604/123 |
| 5,382,227 | 1/1995 | Riquier ........................ | 604/4 |
| 5,407,425 | 4/1995 | Werner et al. ................ | 604/4 |
| 5,411,705 | 5/1995 | Thor et al. .................... | 604/4 |
| 5,411,706 | 5/1995 | Hubbard et al. .............. | 422/46 |

FOREIGN PATENT DOCUMENTS

| | | | |
|---|---|---|---|
| 0 320 815 A2 | 6/1989 | European Pat. Off. ......... | A61M 1/36 |
| 0 583 148 A2 | 2/1994 | European Pat. Off. ......... | A61M 1/36 |
| 43 26 886 A1 | 2/1995 | Germany ...................... | A61M 1/00 |

*Primary Examiner*—John G. Weiss
*Assistant Examiner*—Dennis Ruhl
*Attorney, Agent, or Firm*—Harold R. Patton; Peter Forrest; Curtis D. Kinghorn

[57] ABSTRACT

A perfusion system incorporating a sealed reservoir in communication with a pump which allows any negative pressure at the suction inlet of the pump to be communicated into the reservoir and thereby communicated to any lines connected to the sealed reservoir. The sealed reservoir provides filtration and defoaming elements. An oxygenator and a heat exchanger may be connected to the outlet of the pump to prepare the blood for return to the patient. A control system which operates clamps and displays pressure, temperature, fluid level, and other information measured at various points in the perfusion system, is utilized with a perfusion system. In another embodiment, a hard-shell reservoir utilizing an outlet located at the bottom of the reservoir, said outlet having integral to that outlet a floating ball valve, to where the valve will be opened if there is fluid in the reservoir and closed if no fluid exists in the reservoir.

26 Claims, 7 Drawing Sheets

PERFUSION SYSTEM

BACKGROUND OF THE INVENTION

1. Field of the Invention

The present invention relates to a perfusion apparatus (heart/lung machine) used during open heart surgery, liver transplants, repairs of the aorta, and other surgical or emergency procedures that require the use of an extra corporeal device. More particularly, the present invention relates to a semi-automatic perfusion machine.

2. Description of Related Art

In many surgical procedures, the functions of the heart and lungs are performed outside of the body by specialized devices such as membrane oxygenators, cardiac assist pumps and heat exchangers. This array of equipment is operated by a perfusionist who supervises the removal and return of the patient's blood during the procedure.

Prior art devices used for regulating and processing blood taken from a patient have had a number of disadvantages. Historically, gravity has been used for drawing blood from the patient into a storage container, said storage container being either a hard or soft-shelled reservoir. Gravity procedures require that the reservoir be placed below the level of the patient near the floor. This is done to facilitate the siphoning of blood from the patient to the reservoir. Thus, increasing venous return (de-oxygenated blood leaving the patient) may require raising the patient and operating table, resulting in a need to lengthen the perfusion circuit and add prime volume for the conduits that lead from the operating table down to the reservoir and back to the patient. With prior art systems, the pump was required to generate incremental pumping energy to overcome the hydrostatic head of at least three feet, in addition to energy needed for the rest of the extracorporeal circuit resistance and patient pressure.

An additional disadvantage of the prior art devices just discussed is that the priming volume for the conduits from the table down to the heart/lung machine and back, along with the volumes required for the separate reservoirs, pumps, and interconnecting tubing can end up being a large volume, sometimes two to two and a half liters. Such volume acts to dilute the patient's own blood supply. As such, hemoconcentration of the patient and a significant amount of additional blood, or both, may be required to support the patient. In addition, all the additional conduit material increases the foreign surface area that the blood comes in contact with. Such contact with foreign surface area has been reported to cause damage to the complement, coagulation, and immune system of the patient.

During surgical procedures a significant amount of the patient's blood is lost as a result of bleeding into the chest cavity. The prior art perfusion devices used separate suction devices for recovery of this blood from the operative field, i.e., cardiotomy suction. Blood recovered from cardiotomy suction was in some prior art devices fed into the reservoir. These separate suction devices have been unable to recover and process the shed blood without causing irreversible damage to the formed and unformed elements of the blood.

After blood has been removed from the patient, either through the venous return line, cardiotomy suction or otherwise, it must be directed to an oxygenator, heat exchanger, and filter before being returned to the patient. Bubbles and gross air may be entrapped in the blood that comes from cardiotomy suction and from the venous return line. Such air must be removed before the blood can be safely returned to the patient. A particular problem encountered with past systems that have utilized unsealed reservoirs or, in other words, reservoirs that are open to atmospheric pressure, is that the perfusionist must ensure a minimal blood level in the reservoir in order to prevent gross air from entering the arterial circuit.

In the unsealed reservoir prior-art systems, the mechanism for bringing blood into the reservoir, i.e, either cardiotomy suction or the gravity fed venous return line is completely separate from the mechanism that drains blood from the reservoir, i.e, the pump. It was therefore the perfusionist's job to ensure that in-flow met out-flow in such a way that the blood level in the reservoir did not completely empty, thereby allowing gross air to enter the pump. Therefore, the perfusionist had to constantly increase or decrease the pump output, or increase or decrease the flow from the patient by opening or closing clamps to the venous return line, to maintain a minimum blood level in the reservoir. If gross air entered the pump from an empty reservoir, the perfusionist had to stop the pump and then reprime the system to force the air back into the reservoir before restarting pumping.

In prior art systems, the perfusionist was usually required to use manually operated clamps to control the perfusion circuit along with a pump controller that controlled the output of the reservoir through the pump. Because prior art unsealed reservoirs required constant monitoring, an undesirable situation was created when the perfusionist must perform sampling and other duties throughout the procedure which necessarily diverted the perfusionist's attention away from the perfusion circuit.

The objective of all perfusion apparatus is to ensure that the patient's blood supply is removed, oxygenated, cooled and/or heated and pumped back into the patient in the least traumatic and safest way possible. Therefore, it is evident that there exists a need for a perfusion system that requires a small priming volume, utilizes less foreign surface area, provides fail-safe protection from air being returned to the patient and requires relatively less attention from the perfusionist.

SUMMARY OF THE INVENTION

The present invention provides a perfusion apparatus that improves the regulation of blood flow during surgery or emergency procedures, minimizes priming volume, minimizes foreign surface contact, minimizes pumping pressure requirements and is safe and easier to use. In one embodiment, the invention includes a sealed reservoir that allows air entrapped within the blood supply from a patient to separate from the blood and thereafter by prevented from returning up the venous return line or out-flowing from the reservoir itself into a patient's vascular system. In a further embodiment, the reservoir can be connected to or made integral with a pump. These embodiments are not mutually exclusive and may be incorporated together into a single unit.

In a preferred embodiment, the reservoir incorporates a sealed hard shell reservoir with an integral blood pump mounted vertically below the reservoir. The blood pump may be of any variety. However, a centrifugal is preferably used as the pump.

The term "sealed reservoir" as used in the context of the present invention means that the reservoir is sealed airtight in such a way that any negative pressure created at the inlet of the pump is and can be communicated directly to the reservoir, distributed there throughout and therefore communicated through any conduits connected to the reservoir.

The perfusionist may, for reasons to be discussed later, increase the pressure in the reservoir above the negative pressure created by the pump by opening the reservoir to atmospheric pressure or decrease the pressure in the reservoir below that of the negative pressure created by the inlet of the pump by opening the reservoir to a vacuum source. Because of the sealed nature of the reservoir, the pressure within the reservoir may be controlled at all times by the perfusionist.

The reservoir is filled from a primary venous return line that brings unoxygenated blood from the patient. The venous return line in the preferred embodiment enters the top of the reservoir. Such entry conduit is connected to a one-way valve at its distal end to prevent retrograde flow of venous blood and preclude the passage of air from the reservoir to the patient through the venous return line if the reservoir were to be brought to a pressure greater than that of a patient's own venous pressure. Throughout this disclosure, distal means furthest from the point of reference and proximal means closest to the point of reference.

The reservoir, at its exit, has a floating ball valve that is designed so that the ball will seat if there is insufficient fluid in the reservoir to maintain the ball's buoyancy. Therefore, air will be prevented from leaving the reservoir and entering the pump where it could be passed on toward the patient. As will be apparent to those skilled in the art, any valve that will remain open when substantial fluid exists in the reservoir and close when a minimum amount of fluid is left in the reservoir would suffice. As further protection against air entering the patient's blood stream, during normal operation, any gross air or entrained air that may enter or be contained in the pump may be eliminated by stopping the pump so that the air in the pump can flow up toward the reservoir.

By design, pumps create positive pressure on the outlet and negative pressure on the inlet to the pump. This negative pressure is transferred to the perfusion circuit through the fluid in the reservoir and the venous line. In the preferred embodiment, with the pump directly connected to or integral with the reservoir, the negative pressure of the pump is contained in the sealed reservoir and that negative pressure is then used to facilitate venous flow without hydrostatic or syphon requirements.

The blood may be removed from the patient through one or more cannulae inserted into blood vessels or chambers of the heart of the patient. This blood is free of debris from bone or tissue that is often present in, for example, a patient's chest cavity during surgery. The blood passes from the cannula into the venous return line to the sealed reservoir because of the small amount of suction the pump creates within the reservoir while it is pumping. It is because of this feature that the device can be placed near the patient and at his or her level, thus eliminating the long lines of tubing necessary for prior art devices. Eliminating the long lines of tubing reduces the foreign surface area that the blood necessarily contacts, as well as reduces the necessary priming volume.

The sustained negative pressure within the reservoir created via the pump is communicated to the venous return line via an unfiltered connection site to which the tubing of the venous return line is connected. An unfiltered connection site is one where the connection feeds fluid directly into the mixing chamber where the fluid mixes with blood from the various return lines. This connection site is unfiltered because the blood is free from debris. The negative pressure in the reservoir causes the movement of blood from the cannula (high pressure) to the reservoir (low pressure).

Other connection sites are preferably filtered connections because fluid entering these sites may come from areas where debris may mix with the blood. One example of such an area is the chest cavity where the blood may be contaminated by bone fragments or other tissue as a result of the process of opening the patient's chest for surgery. This blood is brought through filter and defoamer materials before mixing with the blood coming from the venous return line. Such filtered connection sites remove bubbles and debris in the blood. Consequently, such sites are particularly well adapted for use in left ventricular sumps or for cardiotomy suction, as well as for other means.

Traditionally, cardiotomy suction has been separately provided by roller pumps that potentially pull a strong vacuum. This not only introduces additional pumps into the system, but involves the use of a more blood-destructive roller pump. The present system using a centrifugal pump or other pump with less negative pressure at the inlet than a roller pump will provide a more gentle suction action to be used with cardiotomy suction. This is desirable because the gentle suction will provide less velocity and turbulence of the blood than does a relatively stronger suction. Such a system also reduces the number of pumps needed to effect the extracorporeal circulation from two to one.

Blood retrieved by cardiotomy suction from the patient's chest cavity or heart or both enters the reservoir through the connection sites that may or may not be filtered sites depending on the cleanliness of the blood. If the blood needs to be filtered, the blood passes through a filter and a defoamer before entering the main mixing cavity of the reservoir. In the main cavity, venous blood is mixed with cardiotomy blood sources and other miscellaneous blood sources. The mixture is then passed through defoamers before passing on to the outlet of the reservoir. In addition, simply by having a reservoir with slightly negative pressure, entrained air and gross air tend to be removed out of the blood and moved upward into the upper parts of the reservoir.

A variable pressure source can be connected to a port on the sealed reservoir. If the need arises, the pressure within the reservoir can be brought to a value lower than that provided from the suction of the pump. This can be done by opening the reservoir to a vacuum source. As a result of increasing the negative pressure in the reservoir, the rate of drawing blood from the patient will be higher than the rate resulting from just the negative pressure generated by the pump. As a result of the greater negative pressure, the level of blood in the reservoir will increase resulting in a net removal and sequestration of blood from the patient.

When the volume of blood removed, or any volume including the blood removed from the patient and additional fluids added to the reservoir, needs to be given back to the patient, the pressure within the reservoir can be brought to a value higher than the suction of the pump. This can be done by opening the reservoir to the atmospheric pressure. With the relatively higher air pressure in the reservoir, relatively more blood will be taken from the reservoir through the pump and on to the patient than is being brought into the reservoir. This will cause the fluid level in the reservoir to drop.

Finally, an extra volume of blood or balanced electrolyte solutions may be given to the patient from outside sources by connecting the source fluid to a filtered or unfiltered connector on the reservoir. This puts the added fluid in communication with the suction created in the reservoir by the pump.

While the blood passes through the reservoir, any air that is entrained in the venous return line from cardiotomy suction, left ventricular suction, outside fluid source or by other means will be eliminated from the blood in the relatively large, i.e., large relative to the area of the tubing, expanse of the reservoir.

Another embodiment of the present invention includes the use of the hard-shelled reservoir as an unsealed reservoir but still incorporates the floating ball valve at the bottom. As such, when the volume of fluid in the reservoir is depleted, the ball valve will seat, and no air from the reservoir will enter the pump. The pump may continue to pump thereby pulling a gentle vacuum against the ball valve until fluid refills the reservoir. At that point, a brief stoppage of the pump will release the ball to float up with the buoyancy of the fluid and the pump may be simply restarted because there will be no air in the system. In prior systems, the perfusionist would have had to back-fill the pump, the tubing, and the reservoir prior to restarting the system to eliminate any air that had exited from the reservoir once the fluid level was depleted.

In a further preferred embodiment of the present invention, an electronic control panel is utilized to operate electrically or pneumatically controlled clamps can be placed on critical tubes throughout the perfusion system to control the entire perfusion system. In addition to the remotely controlled clamps, the control panel utilizes sensors such as pressure, temperature, fluid level, etc., to feed back information to the control panel for display to the operator. As will be apparent to those skilled in the art, some aspects of control may then be made automatic.

DETAILED DESCRIPTION OF THE PREFERRED EMBODIMENT

The present invention relates to a perfusion system used in performing surgeries or procedures when blood is removed from and returned to the patient. Throughout this description, like elements are referred to by like reference numbers. In a preferred embodiment, shown in FIG. 1, a perfusion circuit 10 is shown having a sealed reservoir 12, a pump 14, an oxygenator 16 and a heat exchanger 18. Blood passes from a cannula 20 in a patient's vein or heart to a cannula 22 in an artery or aorta through reservoir 12, pump 14, oxygenator 16 and heat exchanger 18.

Figure 2:
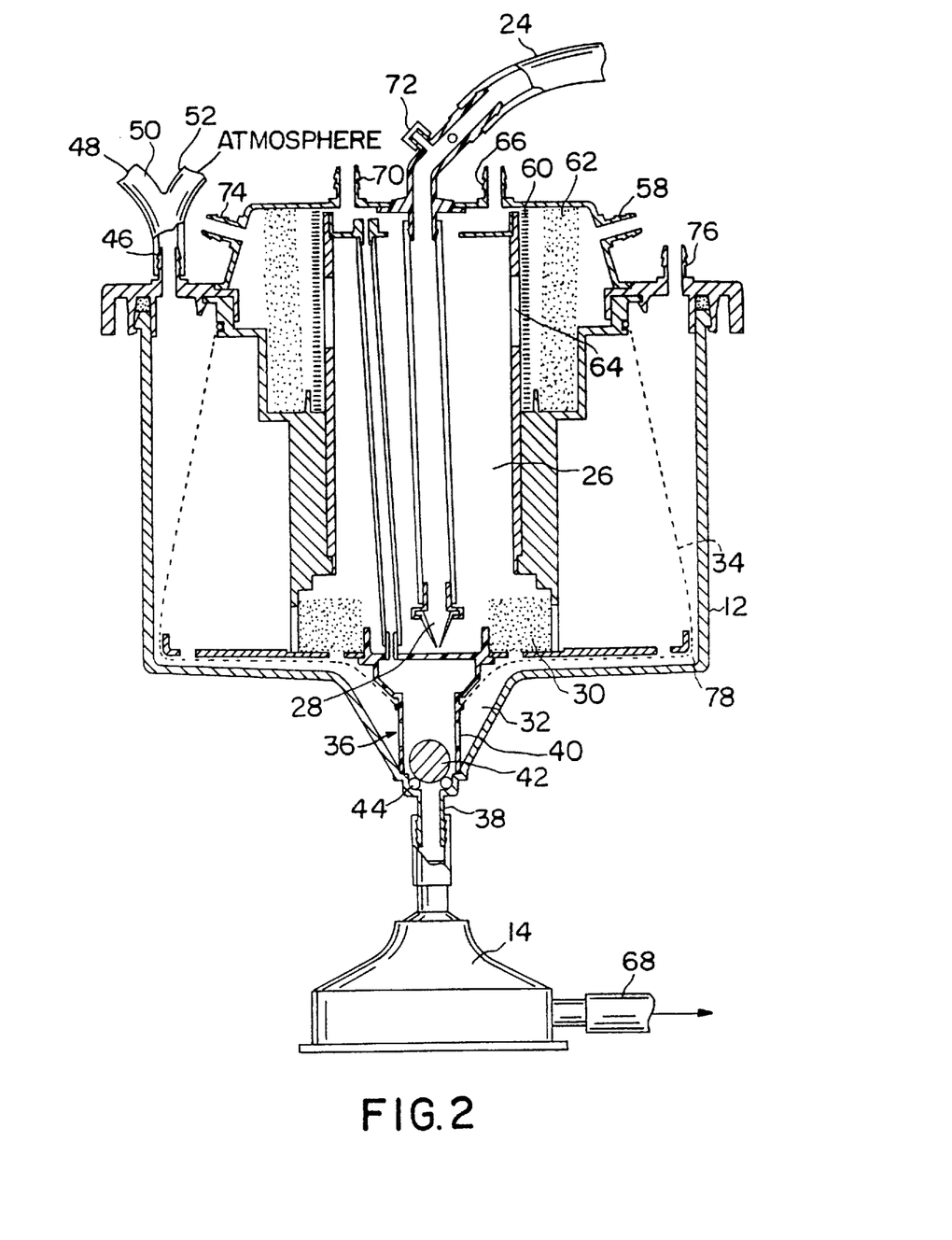
FIG. 2 is a cross-section view of a preferred embodiment of the sealed reservoir and attached pump of the present perfusion system.
Figure 3A:
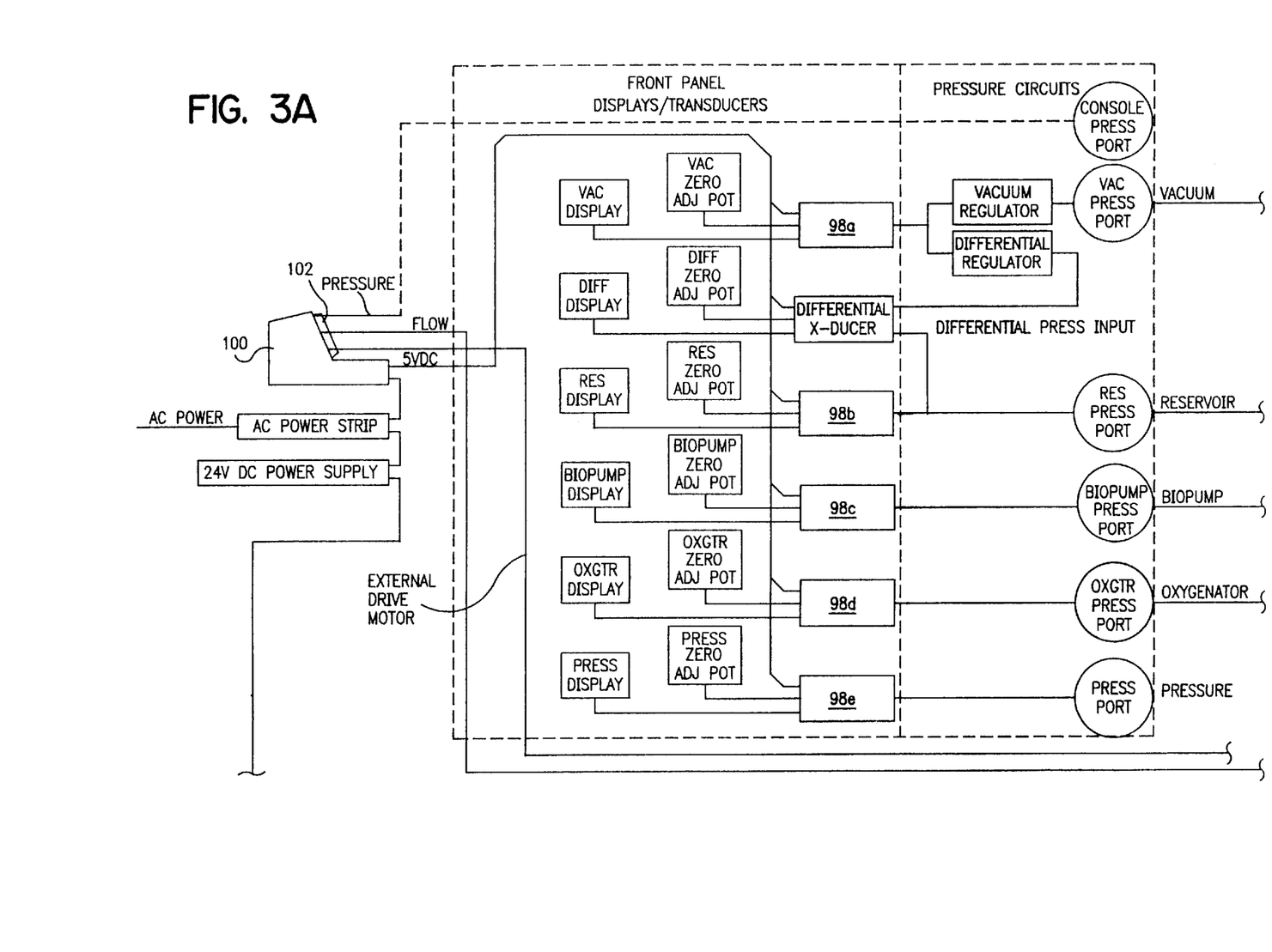
FIG. 3 is a block diagram of a preferred embodiment of the control system of the present invention.
Figure 3B:
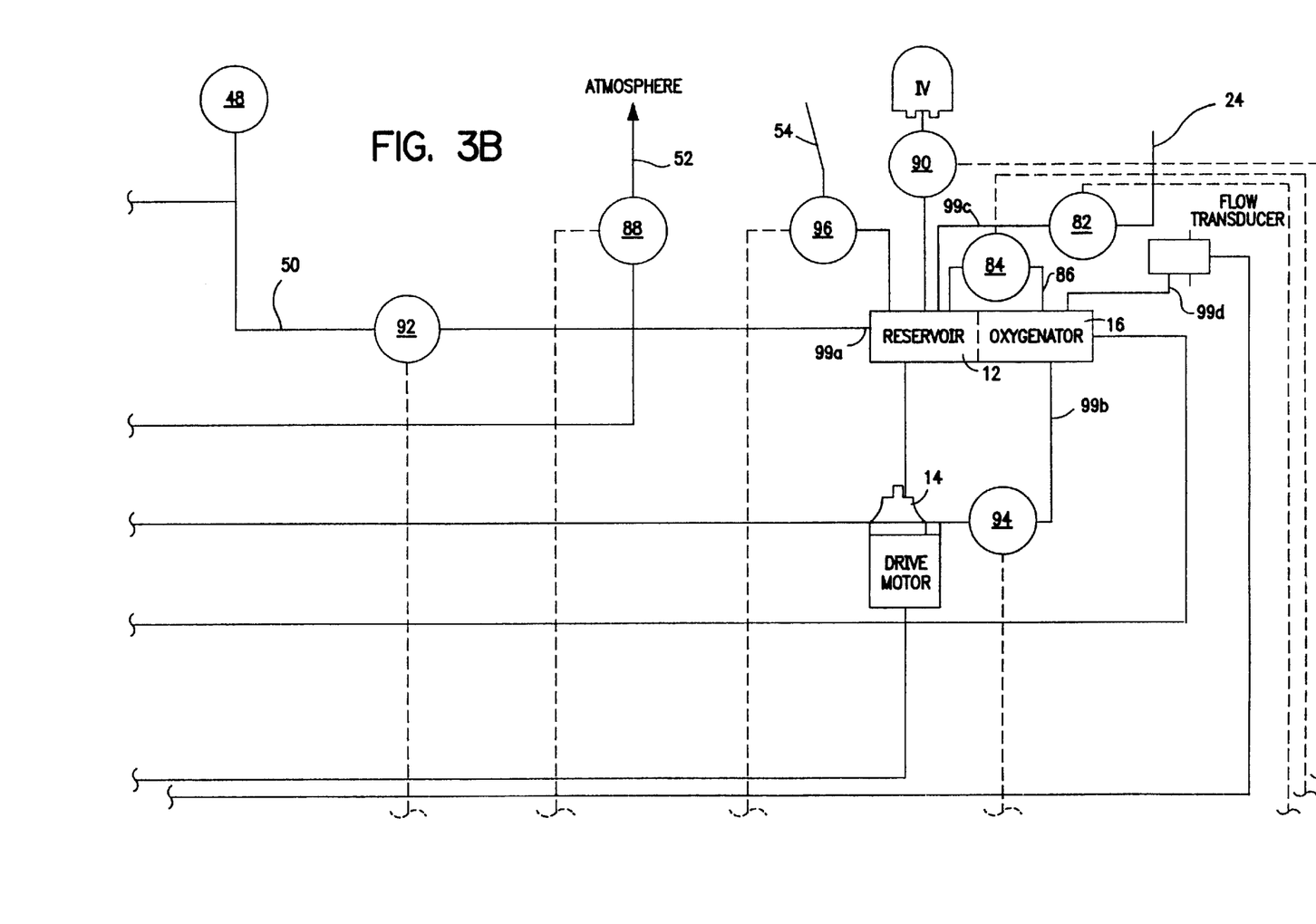
Figure 3C:
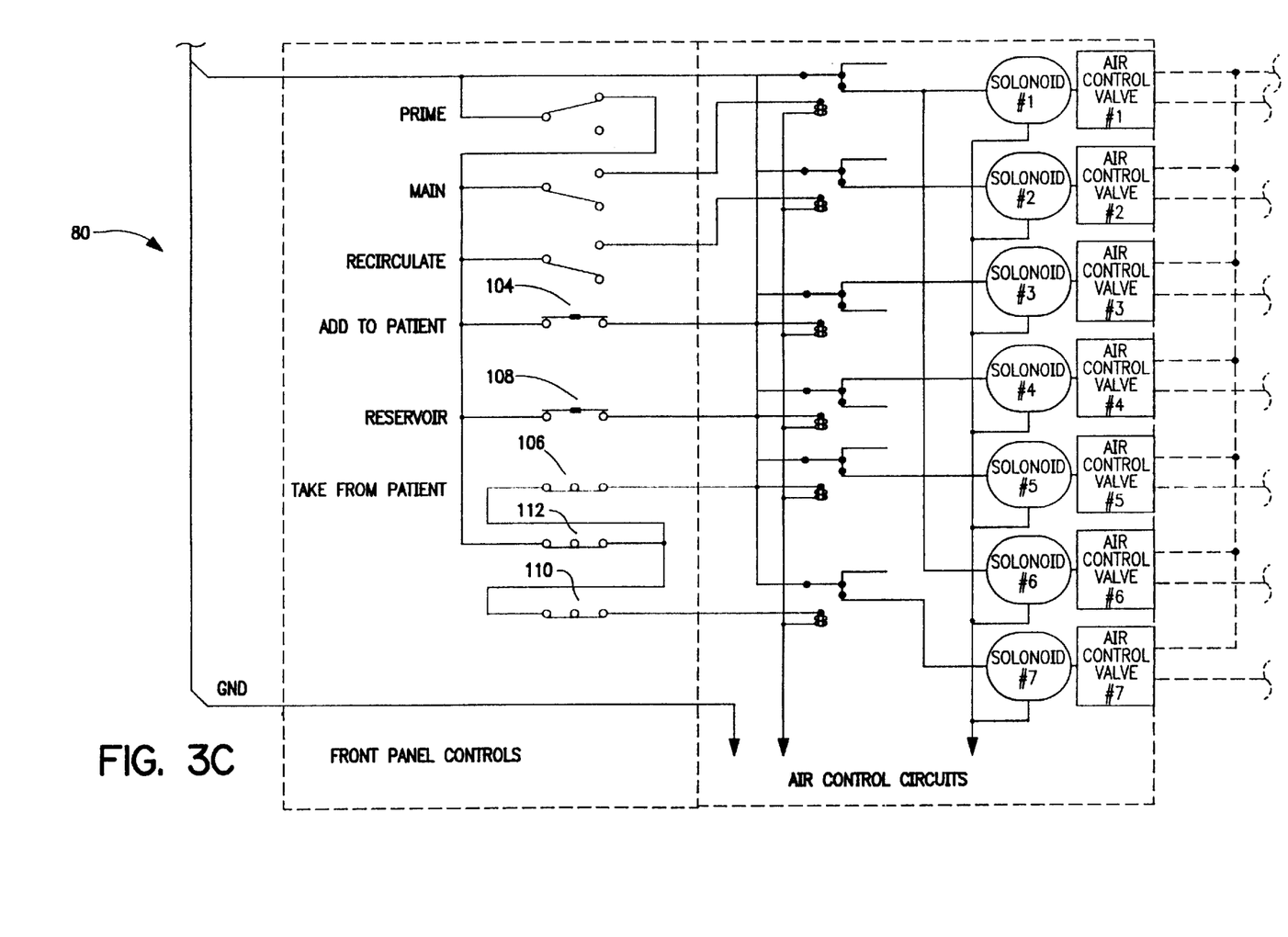
Figure 3D:
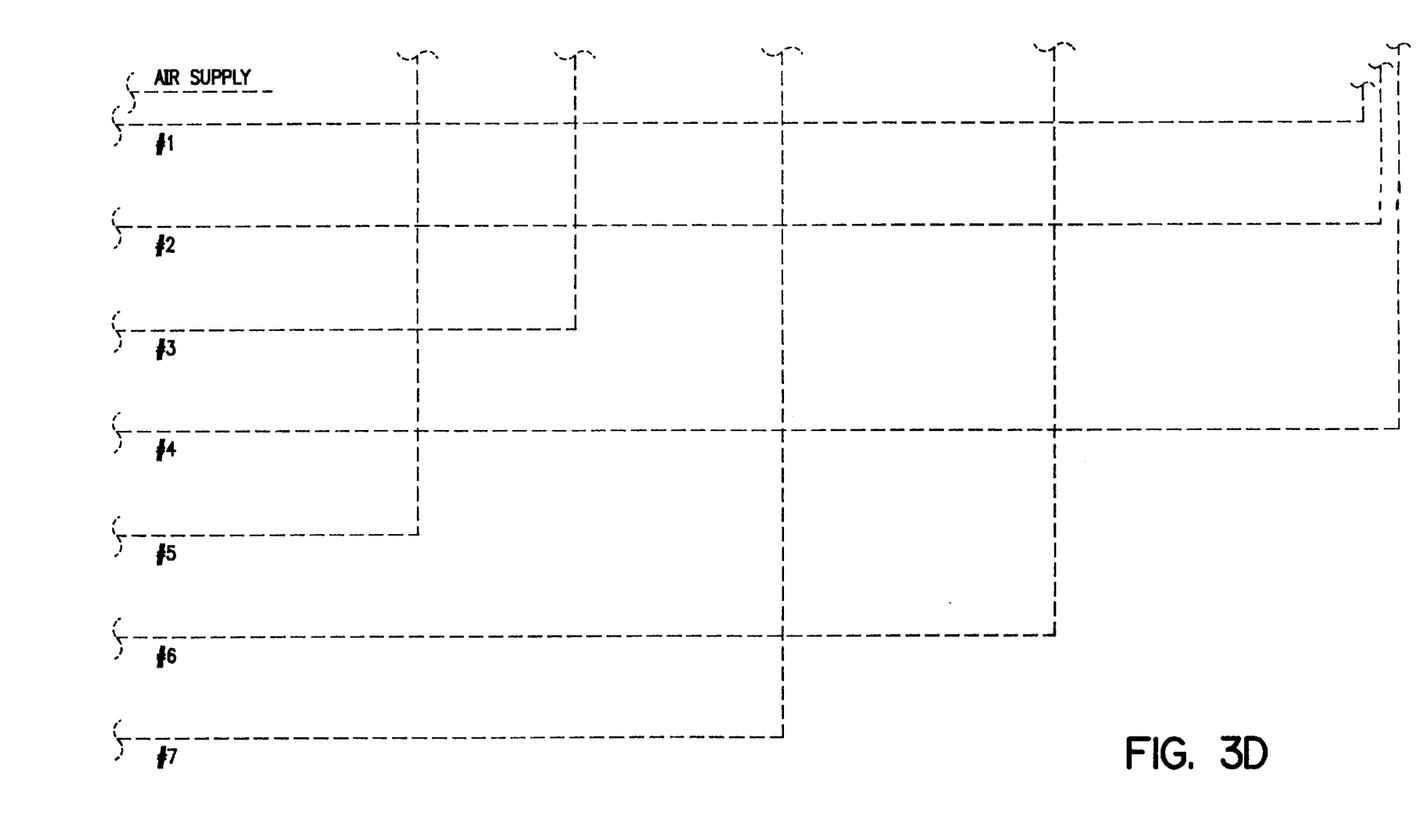

Referring now to FIG. 2, a sealed reservoir 12 and centrifugal pump 14 of the preferred embodiment of the present invention is shown.

A cannula 20 is generally inserted into a vein or chamber of the heart so that blood flows to the perfusion reservoir 12 through the venous return line 24. The blood passes from venous return line 24 into the mixing chamber 26 through a one-way valve 28 at the end of venous return line 24. One-way valve 28, in the preferred embodiment, is a duckbill valve such as is manufactured and distributed by American Omni, Inc. of Irvine, Calif. Although one-way valve 28 is preferable a duck-bill valve, any type of one-way valve may be used. An example of another such one-way valves is, but is not limited to a spring loaded seating valve. One-way valve 28 prevents retrograde flow of blood from reservoir 12 back toward the patient. Additionally, one-way valve 28 prevents air within reservoir 12 from flowing in a retrograde direction to the patient should pressure within reservoir 12 ever exceeds patient venous pressure. Air that may enter the mixing chamber 26 from the venous return line 24 will be dissipated to the top of reservoir 12. The dissipation of the air in reservoir 12 is enhanced by the sub-ambient pressure in reservoir 12 compared to the pressure in the blood.

Blood passes from the mixing chamber 26 through a defoamer 30 and filter screen 34 before being passed through a mixed chamber 32. Defoamer 30 is preferable a polyurethane open cell silicone antifoam although defoamer 30 may also be any biocompatible material with a large surface area. Filter screen 34 is preferably a sock-like enclosure made of a nylon trico material.

Blood, having previously had any air present removed in chamber 26, leaves the mixed chamber 32, and therefore reservoir 12, through a floating ball valve 36. Ball valve 36 may be of the type manufactured by Healthdyne Cardiovascular, Inc. of Costa Mesa, Calif. Blood leaves ball valve 36 through line 38 and passes to centrifugal pump 14. In ball valve 36, an opening 40 allows blood in mixed chamber 32 to pass into ball valve 36. Ball valve 36 includes a ball 42 designed to float or be buoyant in blood or blood products and will seat on site 44 if insufficient blood remains in ball valve 36 to continue to float the ball 42. Ball 42 will seat on site 44 only after virtually all the blood has been removed from chamber 26. Site 44 is preferably an O-ring to provide a sealed seat for ball 42 to rest on. When ball 42 is seated on O-ring 44, no air may pass from reservoir 12 into pump 14 through line 38.

In the preferred embodiment, pump 14 is a centrifugal pump that utilizes smooth conical impellers. Such a pump is manufactured and distributed as a Biopump BP-80 by Medtronic Bio-Medicus, Inc., 9600 W. 76th Street, Eden Prairie, Minn. While a centrifugal pump is preferred for pump 14, any pump that pulls a suction at its inlet could be used with the present invention. Examples of such pumps include, but are not limited to peristaltic or "roller" pumps. With the preferred centrifugal pump 14, air that gets into pump 14 may be eliminated from pump 14 by stopping pump 14, thereby allowing the air to rise from pump 14 through line 38 into ball valve 36 and into reservoir 12 where it will separate from the blood contained therein.

Not shown is the controller that controls pump 14. Such a controller, with a centrifugal pump, provides the turning power and RPM control for pump 14. Furthermore, to enhance the buoyancy effects of the floating ball valve 36, the external dimensions of reservoir 12 are preferably approximately four inches in diameter and eighteen inches high for a reservoir 12 to be used on an adult. As will be clear to those skilled in the art, these dimensions are approximate and may be varied as needed or desired. In addition, these dimensions will be smaller for a reservoir 12 to be used on a pediatric patient.

Reservoir 12 is preferably sealed and requires all ports to be actively occluded or connected to the patient in order to maintain the desired pressure inside reservoir 12. The pressure in mixing chamber 26 is in complete communication with mixed chamber 32. Therefore, the pressure everywhere within reservoir 12 is the same. The fluid level in the mixed chamber 32 is held constant, or nearly so, as long as reservoir 12 is sealed and the subambient pressure generated by pump 14 is maintained. However, the fluid level within reservoir 12 can be altered by using pressure differentials between site 46 and the suction pressure generated by pump 14 at ball valve 36. The pressure differentials can be used to add volume to the chamber 32 by taking volume from the patient, or they can be used to remove volume from the chamber 32 and thereby give volume back to the patient.

A vacuum source 48 attached to reservoir 12 may be controlled so that the pressure in line 50 is lower than in reservoir 12. The reservoir pressure can be measured anywhere within mixing chamber 26 or mixed chamber 32. When the greater negative pressure in line 50 is communicated via site 46 to reservoir 12, volume from the patient will be added to reservoir 12.

If volume in reservoir 12 is to be given back to the patient, site 46 is communicated to atmospheric pressure via line 52. The pressure in reservoir 12 is then greater than the pressure in pump 14. This causes volume to leave reservoir 12 through the oxygenator 16, heat exchanger 18 and cannula 22.

Blood spilled into the operative site in the patient's body during the operation is brought back to reservoir 12 by way of cardiotomy suction. This is done by connecting a suction line 54 ending in a sucker tip 56 to site 58. The sucker tip 56 at the end of suction line 54 is placed below the level of blood in the operative field. Suction line 54 is thereby exposed to the gentle suction contained within the sealed reservoir 12. The blood passes through sucker tip 56 and suction line 54 to site 58 through filter 60 and defoamer 62 and enters mixing chamber 26 through opening 64. Defoamer 62 is preferably a polyurethane open cell antifoam material but may also be any other type of defoamer as will be well understood by those skilled in the art. Filter 60 is preferably a forty micron filter made of a non-woven felt material but may also be any other type of filter for removing debris from blood as will be well understood in the art. Site 58 is a filtered connection because fluid entering there is filtered before mixing with the venous return blood in chamber 26. In the mixing chamber 26, the cardiotomy blood is mixed with the blood and fluids in chamber 26 before being passed through defoamer 30 into the mixed chamber 32. Air that may be brought back with the cardiotomy blood through line 54 or through the venous return line 24 is separated from the blood in reservoir 12 by allowing the air to dissipate to the top of reservoir 12.

In a preferred embodiment the defoamer foam material of 30 and 62 are sprayed with a silicon antifoam such as Antifoam A®, made by Dow Corning, to enhance defoaming capability. In addition, all surfaces in perfusion circuit 10 that will contact blood are preferably coated with a covalent heparin bonding material such as CARMEDA® Bioactive Surface Material sold by Medtronic, Inc. of Minneapolis, Minn. The covalent heparin bonding material increases the biocompatability of any surface of perfusion circuit 10 that may come into contact with blood, thereby reducing clotting.

Often blood lost during surgery cannot be recovered. Balanced electrolyte solution or an outside supply of blood is used to make up for the blood lost. When additional fluids are required, they are added via conduit tubing that delivers the fluid into an unfiltered site 66 of reservoir 12 that empties into mixed chamber 32. The added fluid is then mixed with the patient's blood and is delivered to the patient.

In the preferred embodiment, centrifugal pump 14 is located below reservoir 12 so that blood from reservoir 12 is supplied to centrifugal pump 14 under hydrostatic pressure during surgery as long as the volume in mixed chamber 32 is great enough to float ball 42. This centrifugal pump 14 creates positive pressure at its outlet site 68 and simultaneously creates a negative pressure at inlet line 38.

Pump 14 is also preferably made integrally with reservoir 12 so that the length of inlet line 38 is minimized. In another preferred embodiment, pump 14, though attached to reservoir 12, is not made integrally with reservoir 12. Pump 14 may also be located a distance from reservoir 12 so that inlet line 38 may have a significant length. The negative pressure, or suction, created by pump 14 is communicated equally throughout reservoir 12 because reservoir 12 is sealed. The suction contained in reservoir 12 causes venous blood flow through venous return line 24 without having to lower reservoir 12 below the patient to create a syphon effect. Since reservoir 12 can now be placed at the level of the patient, shorter lines can be used between cannula 20 and the patient and reservoir 12. This reduces both the prime volume needed to get the perfusion circuit 10 started and also reduces the foreign surfaces that the blood must contact throughout the extracorporeal circuit.

Additional unfiltered ports, such as 70 and 72, may communicate directly with the mixing chamber 26. Additional filtered ports, such as 74, may also exist that allow fluids added to reservoir 12 to pass through defoamer 62 and then through filter 60 before entering mixing chamber 26. These filtered ports 74 could be utilized for additional cardiotomy lines.

Ventricular sumping is achieved by way of connecting a ventricular sumping line 75 to port 76 that provides a gentle suction to cannula 20 placed into the left ventricle of a heart to keep the left ventricle empty. Blood entering reservoir 12 through port 76 bypasses filter 60 and defoamer 62 and passes directly into mixed chamber 32 through opening 78. This system brings the blood back to the unfiltered mixed chamber 32 for re-introduction into the extracorporeal circuit.

Figure 1:
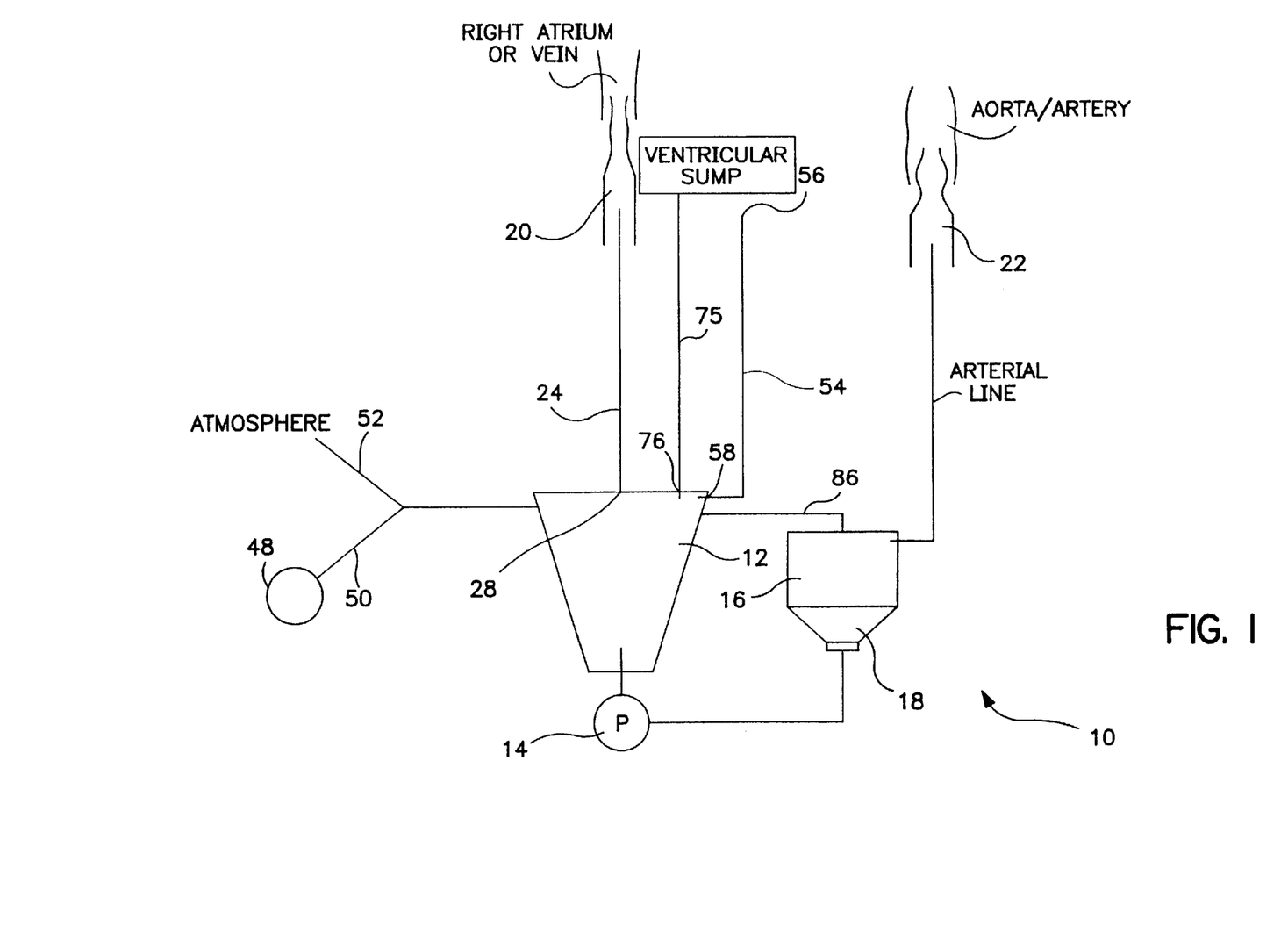
FIG. 1 is a schematic diagram of the perfusion system of the invention.

As shown in FIG. 1, the output from pump 14 is processed through an oxygenator 16 and a heat exchanger 18. The oxygenator 16 and heat exchanger 18 may be provided integrally with pump 14 and reservoir 12. Alternately, either oxygenator 16 or heat exchanger 18 may be made integrally with pump 14 with or without an integral reservoir 12. In another alternate embodiment, oxygenator 16 or heat exchanger 18 may be made integrally with reservoir 12 regardless of whether pump 14 is integral with reservoir 12.

The perfusion circuit 10 of the present invention can also be used for procedures such as thoracic aneurysms and liver transplants. These procedures do not utilize an oxygenator 16 but could benefit from the use of the combined reservoir 12 and pump 14 of the present invention. Because the fluid level in reservoir 12 is essentially constant once established, the use of the combined reservoir 12 and pump 14 of the present invention will provide additional safety beyond simply using a pump system to pull blood from the body and return it back to the patient. In addition, because the perfusion circuit 10 of the present invention can be primed quickly and easily and be ready to apply to the patient in very short order, perfusion circuit 10 may be used for urgent or emergency situations in the cath lab, emergency room, ICU, CCU or hospital room. To prime the perfusion circuit 10 requires simply supplying some prime fluid to the sealed reservoir 12 to establish a minimum fluid level thereby opening ball valve 36. Pump 14 is then turned on and the system, including oxygenator 16, heat exchanger 18 and the rest of perfusion circuit 10 primes itself by movement of fluid from pump 14 through perfusion circuit 10.

The present invention provides a perfusion circuit 10 that may be primed with approximately half the amount of prime volume currently required for prior art systems. In addition, because perfusion circuit 10 can be placed close to the patient thereby reducing the lengths of tubing needed, the amount of foreign surface level contacted during perfusion activities is substantially reduced. Reducing the length of foreign surface contacted by the blood provides less trauma to the blood and reduces clotting.

Finally, because the outlet flow and the inlet flow of reservoir 12 may be made to be the same due to the sealed nature of reservoir 12, the fluid level within reservoir 12 remains virtually constant. Because of the sealed nature of the reservoir 12 and pump 14 system, the fluid level in reservoir 12 is virtually constant and therefore no gross air may enter perfusion circuit 10. This reduces the burden on the perfusionist to try to constantly match in-flow and out-flow to and from reservoir 12. In addition, the perfusion circuit 10 can be set to provide a more constant rate of blood withdrawal and return to the patient, rather than having to fluctuate the output of pump 14 to prevent gross air from entering perfusion circuit 10. Such fluctuation of the flow from pump 14 varies the amount of blood returning to the patient.

Referring to FIG. 3, a preferred embodiment of the control system of the perfusion circuit 10 is shown generally labelled 80. The preferred embodiment of control system 80 includes pneumatically or electrically operated clamps. The first clamp 82 is placed on the venous return line 24. The second clamp 84 is placed on a by-pass line 86 going directly from the oxygenator 18 back to reservoir 12. The third clamp 88 is placed on the atmospheric vent line 52. The fourth clamp 90 is placed on an IV line entering unfiltered site 66 for providing either a balanced electrolyte solution or blood from an outside source. The fifth clamp 92 is placed on the line 50 from vacuum source 48. The sixth clamp 94 is placed on the outlet from pump 14 to oxygenator 16. The seventh clamp 96 is placed on the line 54 used for cardiotomy suction. Although specific arrangements of clamps 82, 84, 86, 88, 90, 92, 94 and 96 have been shown, it is to be understood that other arrangements of these or additional clamps may be used and still be within the intended scope of the disclosed invention.

Pressure transducers 98*a–e* are used to measure the pressure of the vacuum source 48 and the pressure of reservoir 12, pump 14, oxygenator 16 and atmospheric pressure, respectively. Additionally, transducers 99*a–d* can also be used to monitor fluid level in reservoir 12, the flow rate and possibly even detect air or bubbles in either the in-flow or outflow of the perfusion circuit 10, respectively.

A console 100 is designed to display the various data retrieved by transducers 98 and to provide control buttons 102 for the various clamps 82, 84, 86, 88, 90, 92, 94 and 96 as well as some standardized control buttons. For example, there may be a button 104 that, when activated, will control clamps that add volume to the patient to return volume to the patient. In this instance, opening clamp 88 will open reservoir 12 to atmosphere, thereby increasing the pressure within reservoir 12 and forcing more fluid to pump 14.

There could also be a button 106 to initiate a procedure to add volume to reservoir 12 from the patient. This would be accomplished by opening clamp 92 to vacuum source 48 and adding additional negative pressure into reservoir 12, thereby pulling more fluid from the patient.

There could also be a button 108 to initiate a procedure to add prime volume to reservoir 12 from an external source. This would be accomplished by operating clamp 90 to release an IV line so that blood or balanced electrolyte solutions or other medicines or other external fluids may be added to the blood contained in reservoir 12.

Another button 110 may be provided to turn off and on cardiotomy suction. This may be accomplished by pressing button 110 that would cause clamp 96 to open thereby applying suction to sucker tip 56.

Another button 112 may provide cardiotomy suction boost by opening cardiotomy suction clamp 96 to the negative pressure already contained in reservoir 12 by the operation of pump 14 and then boosting or increasing that negative pressure by opening clamp 92 to vacuum source 48. Other preset buttons may be provided in addition to other various displays. The general concept is to provide monitoring of pressures and fluid levels and provide remotely controlled clamps that may be opened and closed in response to control signals from the control system 80 to provide for certain desired results within perfusion circuit 10. The control system 80 of the present invention would also be useful with prior art perfusion systems.

As will be appreciated by those skilled in the art, the use of a reservoir 12 that is not sealed but that still has a ball valve 36 at the base of reservoir 12, between reservoir 12 and pump 14, will provide protection from gross air entering the perfusion circuit. With such a system, precious time may be saved during an operation when reservoir 12 empties of fluid by not allowing air to pass out of reservoir 12 into the perfusion circuit. As such, pump 14 may be restarted as soon as reservoir 12 refills or is refilled with fluid rather than having to purge the system of air and then restart pump 14.

Figure 4:
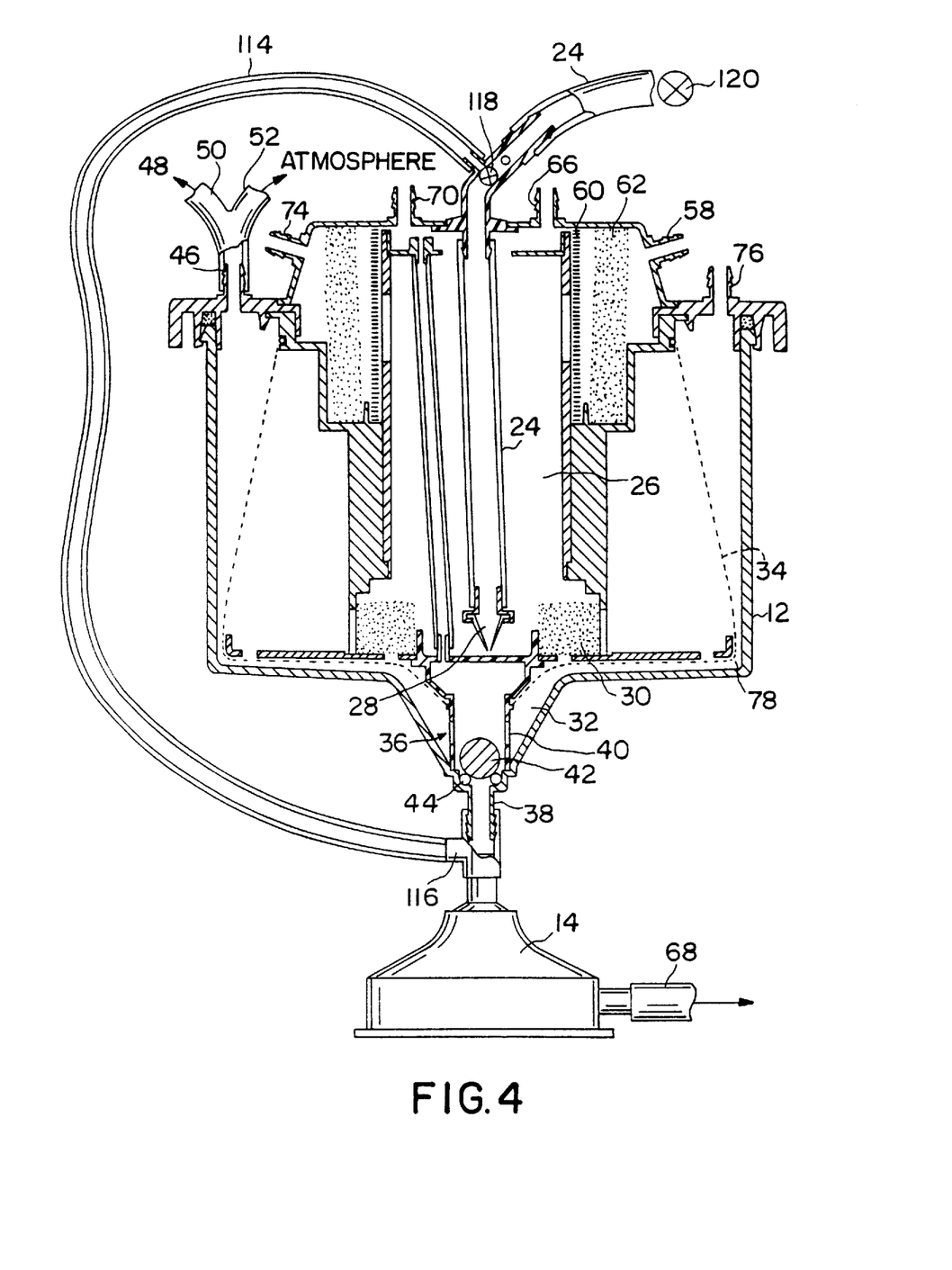
FIG. 4 is a cross-section view of the preferred embodiment of FIG. 2 with the addition of a bypass apparatus.

A further embodiment of the present invention that is directed to further reducing the foreign surface area of the perfusion circuit 10 that the blood must contact provides a bypass around sealed reservoir 12. Referring to FIG. 4, the device shown in FIG. 2 is modified by adding a bypass line 114 that feeds directly from venous return line 24 to a pump intake 116 on pump 14. Bypass line 114 includes a bypass valve 118 at or near venous return line 24 before venous return line 24 connects to reservoir 12. Bypass valve 118 may be operated either manually or automatically. When bypass valve 118 is activated, blood in venous return line 24 is directed through bypass line 114 directly to pump 14 without first entering reservoir 12.

In an embodiment where bypass valve 118 is automatically controlled, an air or bubble sensor 120 may be attached to the venous return line 24. When air or bubble sensor 120 indicates that no air is contained in the venous blood in venous return line 24, the blood is bypassed from venous return line 24 around reservoir 12 and sent directly to pump 14. When the air or bubble sensor 120 indicates that air or bubbles exist in the venous blood in venous return line 24, bypass valve 118 is activated so that the venous blood will enter sealed reservoir 12 from venous return line 24 and go through defoamer 30 and filter 34 and the settling process of sealed reservoir 12 as described above. Such a modification would ensure that during standard operation when no air is included with the venous blood supply in venous return line 24, the blood need only come in contact with the bypass line 114 and not all of the various elements of sealed reservoir 12. In such an embodiment, either when bypassing or when going through sealed reservoir 12, venous return line 24 will always be subject to the suction pressure at the inlet of pump 14, and therefore, perfusion system 10 may still be placed at or near the patient. Therefore, the bypass embodiment also achieves the benefits of reducing priming volume and further reducing foreign surface contact.

The present invention as described provides a safe, easy to use perfusion system that is easier to prime and provides less trauma for blood products than previously known perfusion systems. Although the present invention has been described in connection with several specific embodiments of the invention, it is to be understood that the specific embodiments disclosed have been for the purpose of illustrating the invention. However, the invention is not intended to be limited to the embodiments disclosed. It is clear that changes and improvements to the invention disclosed will occur to those skilled in the art and will still be within the scope of the claims that appear hereafter.

I claim:

1. A perfusion system comprising:

a first line for removing blood from a patient, the first line having a proximal end and a distal end, a sealed reservoir having at least a first connecting site connected to the proximal end of the first line, the reservoir having an interior;

a pump having a pump intake port in fluid communication with the sealed reservoir, the pump being capable of pulling negative pressure at the pump intake port so that the negative pressure is transferred to the reservoir and ultimately to the first line for removing blood from a patient through the first connecting site;

a bypass line connected at one end to the pump intake port and connected, at the other end, to and in fluid communication with the first line so that fluid in the first line can be directed around the reservoir to the pump intake port;

a cannula attached to the distal end of the first line and adapted to be inserted into blood vessels or chambers of a heart;

in which the reservoir further comprises a mixing chamber and the system further comprises a first one-way valve in fluid communication with the first line and the mixing chamber.

2. The system of claim 1 in which the pump is integral with the reservoir.

3. The system of claim 2 in which the pump is attached to the reservoir below the reservoir.

4. The system of claim 1 in which the pump is a centrifugal pump.

5. The system of claim 1 in which the pump is a peristaltic pump.

6. The system of claim 1 in which the reservoir is rigid.

7. The system of claim 1 in which the one-way valve is a duck-bill valve.

8. The system of claim 1 in which the one-way valve is a spring loaded seating valve.

9. The system of claim 1 in which the first connecting site includes a filter for filtering fluid entering the reservoir through the first connection site.

10. The system of claim 9 in which the filter is a forty micron filter made of a non-woven felt material located between the first connection site and the interior of the reservoir.

11. The system of claim 1 in which the reservoir includes a filter screen located in the interior of the reservoir through which blood passes from the first connecting site to the interior of the reservoir.

12. The system of claim 11 in which the filter screen is a nylon tricot material.

13. The system of claim 1 in which the reservoir includes a defoamer located in the interior of the reservoir through which blood passes from the first connecting site to the interior of the reservoir.

14. The system of claim 13 in which the defoamer is a polyurethane open cell silicone antifoam.

15. The system of claim 13 in which the defoamer is coated with a silicon antifoam.

16. The system of claim 1 in which the reservoir includes a port in fluid communication with the interior of the reservoir and the system includes a variable gas pressure source connected in fluid communication with the port.

17. The system of claim 1 further comprising an outlet between the interior of the reservoir and atmospheric air pressure.

18. The system of claim 1 further comprising a second one-way valve located in fluid communication between the reservoir and the pump.

19. The system of claim 18 in which the second one-way valve is a spring loaded seating valve.

20. The system of claim 1 in which the first line is a suction line ending at its distal end in a sucker tip whereby a suction line for cardiotomy suction is created.

21. The system of claim 1 in all surfaces in the system that will contact blood are coated with a covalent heparin bonding material.

22. The system of claim 1 further comprising an inlet for additional fluid from an external source to the reservoir which inlet is separate from the first line attached to the first connecting site.

23. The system of claim 22 wherein the inlet for additional fluid from an external source comprises a second connecting site on the reservoir for connecting a second line for adding fluids to the reservoir, the second line having a proximal and a distal end, the proximal end of the second line attached to the second connecting site.

24. The system of claim 1, in which the bypass line includes a bypass valve, located where the first line and the bypass line are connected, to direct fluid into the bypass line from the venous blood return line depending on whether the bypass valve is activated.

25. The system of claim 24 in which the bypass valve is manually activated.

26. The system of claim 25 further comprising an air or bubble sensor attached to the first line to automatically control the bypass valve.

* * * * *